(12) United States Patent
Yamasaki et al.

(10) Patent No.: US 6,953,442 B2
(45) Date of Patent: Oct. 11, 2005

(54) KNEE BRACE (75) Inventors: Jyunpei Yamasaki, Matsuyama (JP); Takashi Moriwaki, Matsuyama (JP)

(73) Assignees: Yoshitika Motokubo, Matsuyama (JP); Kazuyuki Tanimoto, Matsuyama (JP)

( * ) Notice: Subject to any disclaimer, the term of this patent is extended or adjusted under 35 U.S.C. 154(b) by 131 days.

(21) Appl. No.: 10/287,535

(22) Filed: Nov. 5, 2002

(65) Prior Publication Data
US 2003/0100853 A1 May 29, 2003

(30) Foreign Application Priority Data

Nov. 28, 2001 (JP) ........................................ 2001-402277

(51) Int. Cl.$^7$ ................................................. A61F 5/00
(52) U.S. Cl. ......................................... 602/22; 602/26
(58) Field of Search ..................... 602/23, 26; 128/869, 128/882

(56) References Cited

U.S. PATENT DOCUMENTS

| | | | |
|---|---|---|---|
| 4,649,906 A | | 3/1987 | Spademan |
| 4,697,583 A | * | 10/1987 | Mason et al. ............. 128/80 C |
| 5,330,418 A | | 7/1994 | Townsend et al. |
| 5,419,754 A | | 5/1995 | Hutchins |

FOREIGN PATENT DOCUMENTS

| | | |
|---|---|---|
| EP | 0 173 161 | 3/1986 |
| JP | 6-139 | 1/1994 |
| JP | 3093269 | 10/2000 |
| WO | WO 99/20212 | 4/1999 |
| WO | WO 99/26564 | 6/1999 |

* cited by examiner

*Primary Examiner*—Michael A. Brown
(74) *Attorney, Agent, or Firm*—Oblon, Spivak, McClelland, Maier & Neustadt, P.C.

(57) ABSTRACT

There is disclosed a knee brace having first and second arms constituting a pair of left and right arms fixed to the thigh bilateral sides along the user's femur, and third and fourth arms constituting a pair of left and right arms fixed to the shank bilateral sides along the user's tibia, wherein the lower ends of the first and second arms and the corresponding upper ends of the third and fourth arms are pivotally connected together to provide two pairs of upper and lower arms, so that the third and fourth arms are allowed to pivotally move with a pivotal part as the center correspondingly to the knee motion. Gears and guide grooves respectively having racks meshing with the gears and extending in parallel to a femur or tibia axial center are provided opposite to the ends of the arms constituting the pairs of left and right arms. The arms constituting the pairs of upper and lower arms are pivotally connected together such that gears are allowed to slide in the guide grooves while being in mesh with the racks.

21 Claims, 12 Drawing Sheets

KNEE BRACE

BACKGROUND OF THE INVENTION

1. Field of the Invention

This invention relates to a knee brace, and more particularly, to a knee brace having an improved pivotal joint, which pivotally joins a thigh fixing part and a shank fixing part together, to produce an effect on a corrective treatment according to user's knee troubles.

2. Description of the Related Art

Conventionally, two types of knee-joint corrective knee braces for a case of degenerative knee arthrosis have been available, such as a knee brace characterized by providing a belt in a dog-legged shape as viewed front ways to put the knees to zero-degree positions between valgus and varus by the action of a belt traction force, and a knee brace characterized by providing a shank fixing part having a plurality of straps to impact the shanks in a corrective direction for fixation in place by the action of a strap pressing force.

However, as a result of practical uses, the knee-joint corrective knee brace for the case of degenerative knee arthrosis has had a disadvantage of being incapable of sufficient correction of the knee joints with the belt traction force. In addition, use of the knee brace for tibia correction merely with the straps presents disadvantages of needing a complicated installing work or the like by reason that strap adjustment or the like takes much time because of the use of a large number of straps, and also having little effect of the straps on the tibia correction.

As disclosed in Japanese Patent Publication No. 6-139 and U.S. Pat. No. 3,093,269, knee braces respectively having improved pivotal parts have been recently developed in order to dissolve the above disadvantages. A brace device disclosed in the Japanese Patent Publication No. 6-139 is characterized by providing a hinge device having a guide groove in the shape of a laterally longer slot, wherein upper and lower braces are formed movably in a lateral direction along the guide groove to make a motion in imitation of user's knee flexion.

Inventions disclosed in the U.S. Pat. No. 3,093,269 all relate to a detachable knee brace having an effect of permitting a knee motion to a certain degree, while holding the knees in place surely before and after higher tibia osteotomy. This knee brace is also supposed to be an orthotic device that takes the place of a conventional cast for knee fixation. In the U.S. Pat. No. 3,093,269, there are disclosed three kinds of inventions, that is, the invention characterized by providing a support plate having a shape conformable to a partial circular projection of each of an inside support plate and an outside support plate so as to be put between the inside support plate having the partial circular projection and the outside support plate having the partial circular projection in contact therewith, wherein a bolt is provided sidably in a slot formed in the support plate to unite the inside and outside support plates as one body, and an arm and the support plate having the slot are connected together through a joint having an inclination angle to make an inclination controllable by changing the inclination angle of the joint to a desired angle; the invention characterized by providing a hinge device between outside support plates having circular projections, wherein the hinge device is placed opposite to a knee joint medial portion such that a pair of upper and lower arms is moved pivotally toward a knee lateral side; and the invention characterized by pivotally connecting the arms to upper and lower extending parts of the support plate having the slot to constitute a rotary joint. According to the inventions disclosed in the U.S. Pat. No. 3,093,269, only in a case of knee flexion, in other words, when no load is applied to the knee joints, the pair of upper and lower arms is moved pivotally toward the knee lateral side, so that the bolt is allowed to shift in a protrusive direction of the circular projection-shaped support plate within the slot provided in the above support plate to perform knee traction in vertically opposite directions by the same distance as an amount of movement of the bolt in a height direction of the above support plate. On the other hand, in a case of knee extension, in other words, when a load is applied to the knees in a standing posture, the bolt is allowed to shift downwards to an outside end within the slot to place the pair of upper and lower arms at an angle of approximately 180 degrees, so that an effect of the arms on femur and tibia traction is lost. For this reason, a clearance is produced between the femur and the tibia by the action of the traction force of the arms to alleviate a pain in the knees at the time of knee flexion. On the other hand, since the traction force of the arms is lost at the time of knee extension, the application of the load to the knees occurs to bring a femur surface into contact with a tibia surface without leaving the clearance therebetween. As a result, the user feels the pain in one's knees.

Since the invention disclosed in the Japanese Patent Publication No. 6-139 as described above has the laterally longer slot, the upper and lower braces fixedly installed to the thigh and the shank using the straps are pivotally moved while making a movement by a distance corresponding to the lateral length of the slot. In this case, since neither the slot nor an axis has a portion having an anchoring function, the braces are allowed to move freely, so that the pivotal movement of each brace with a specific position as a center is made impossible. For this reason, the pivotal part in each brace is not stabilized in some cases, resulting in problems of having little effect on a corrective treatment based on traction suitable to a genu varum and a genu valgum and control of a tibia position for a case of ligament disease, for instance, although a degree of freedom of the knee motion is increased.

According to the inventions as disclosed in the U.S. Pat. No. 3,093,269, when the pivotal movement of the arms toward the knee lateral side occurs, the bolt is allowed to slide within the slot formed in the circular projection-shaped support plate to perform the knee traction by the same distance as the amount of movement of the bolt in the height direction of the above support plate so as to produce the clearance in the knee joints only at the time of knee flexion that needs no application of load to the knees, in other words, does not cause pain to the knee joints so much. However, at the time of knee extension that causes pain to the knee joints most severely because of the application of load to the knees, the clearance in the knee joints is lost again to bring the femur surface into contact with the tibia surface. Thus, the knee brace according to the above inventions has no effect of the traction force in the standing posture on valgus rotation at all, and as a result, brings about a situation that the user in the case of degenerative knee arthrosis becomes tired of having the knee braces on for a long period of time, by reason that any pain is not alleviated even though the user makes repeatedly flexion and extension, that is, walks with the knee braces on.

SUMMARY OF THE INVENTION

It is an object of the present invention to provide a knee brace installed to a non-operable knee for a corrective treatment for a case of degenerative knee arthrosis by performing traction of only a required portion using a transmission means such as a gear, a corrective treatment for a case of abnormal rotation combined with the degenerative knee arthrosis by changing the abnormal rotation to a normal rotation while performing the traction, and a corrective treatment for a case of ligament disease by changing an abnormal tibia advancement or retraction to a normal motion.

For attaining the above object, according to the present invention as defined in claim 1, in a knee brace having a thigh fixing part and a shank fixing part respectively for user's femur and tibia fixation in place, wherein the thigh fixing part and the shank fixing part are pivotally connected together through a pivotal joint placed on each of the user's knee bilateral sides in order to permit user's knee flexion, the knee brace is characterized by providing the pivotal joint having at least one means among a means for femur and tibia traction in vertically opposite directions against a user's knee joint medial and/or lateral portion, a means for control and correction of a rotation in a femur-to-tibia joint and a means for correction of a tibia position to the femur by adjusting the tibia motion in a case of knee extension.

According to the present invention as defined in claim 2, in a knee brace having first and second arms constituting a pair of left and right arms fixed to the thigh bilateral sides along the user's femur, and third and fourth arms constituting a pair of left and right arms fixed to the shank bilateral sides along the user's tibia, wherein the lower ends of the first and second arms are pivotally connected to the corresponding upper ends of the third and fourth arms to provide two pairs of upper and lower arms so that the third and fourth arms are allowed to pivotally move with the pivotal part as the center correspondingly to the user's knee motion, the knee brace is characterized in that the knee brace further has a gear and a guide groove having a rack meshing with the gear and extending in parallel to the user's femur or tibia axial center, wherein the gear and the guide groove are provided opposite to the end of each of the arms constituting the pair of left and right arms, and the arms constituting the pair of upper and lower arms are pivotally connected together such that the gear is allowed to slide within the guide groove while being in mesh with the rack.

According to the present invention as defined in claim 3, the knee brace is characterized in that the knee brace further has an upper arm fixed to the thigh side along the user's femur, a lower arm fixed to the shank side along the user's tibia, a connection plate having a rack mounted in parallel to the guide groove and an elastic piece, wherein a gear formed at each of the lower end of the upper arm and the upper end of the lower arm is pivotally mounted so as to be in mesh with the rack, and the opposite ends of the elastic piece are allowed to slidably make contact with pivots of the pivotal part to energize the ends of the pair of upper and lower arms connected together through the connection plate so as to be apart from each other.

According to the present invention as defined in claim 4, the knee brace is characterized in that the guide grooves respectively having the racks are inclined in the longitudinally opposite directions at the same inclination angle.

According to the present invention as defined in claim 5, the knee brace is characterized in that the gear has different root radius portions and/or portions different in circumferential tooth pitch, and the rack is provided at different levels and/or has tooth portions different in tooth pitch correspondingly to the circumferential tooth pitch of the gear.

According to the present invention as defined in claim 6, the knee brace is characterized in that the gear includes a plurality of concentric gears different in circumferential tooth pitch, and the rack has different level portions formed correspondingly to a difference in root radius between the gears and also having tooth portions formed at the same tooth pitch as the circumferential tooth pitch of the gear meshing with the rack.

According to the present invention as defined in claim 7, the knee brace is characterized in that a pair of gear mounting pieces facing each other is provided as a result of downwardly extending the left and right sides of a thigh holding part capable of accommodation of the user's thigh on the inside so that gears are fixedly mounted to the opposite positions on the outsides of the gear mounting pieces, while a pair of guide groove formation pieces is provided as a result of upwardly extending the left and right sides of a shank holding part capable of accommodation of the user's shank on the inside so that a guide groove having a rack is mounted to each guide groove formation piece in a direction orthogonal to a user's tibia axial centerline, and each gear is mounted in the guide groove so as to be capable of sliding within the guide groove while being in mesh with the rack.

According to the present invention as defined in claim 8, in a knee brace having first and second arms constituting a pair of left and right arms fixed to the thigh bilateral sides along the user's femur, and third and fourth arms constituting a pair of left and right arms fixed to the shank bilateral sides along the user's tibia, wherein the lower ends of the first and second arms are pivotally connected to the corresponding upper ends of the third and fourth arms to provide two pairs of upper and lower arms so that the third and fourth arms are allowed to pivotally move with the pivotal part as the center correspondingly to the user's knee motion, the knee brace is characterized by providing a first projection and a second projection on each of the outsides of the upper ends of the third and fourth arms at a predetermined distance, and a first guide groove and a second guide groove in each of the lower ends of the first and second arms to respectively allow the first and second projections to slide along the inside, wherein the first guide groove is formed in the shape of a slot extending linearly in one of the longitudinal and lateral directions, while the second groove is formed in the shape of a slot composed of a semicircular portion extending in a semicircular shape from one base end and a curved portion curved inwardly from a bent portion, and an angle $\theta$ made by one base end of the second guide groove and the bent portion with the other base end of the first guide groove as the center is set to agree with an extension angle that causes pain to the user's knees most severely at the time of knee extension in a case of shifting the state of the knees from flexion to extension.

BRIEF DESCRIPTION OF THE DRAWINGS

The foregoing and other objects and features of the invention will become apparent from the following description of preferred embodiments of the invention with reference to the accompanying drawings, in which.

DETAILED DESCRIPTION OF THE PREFERRED EMBODIMENTS

Figure 1A:
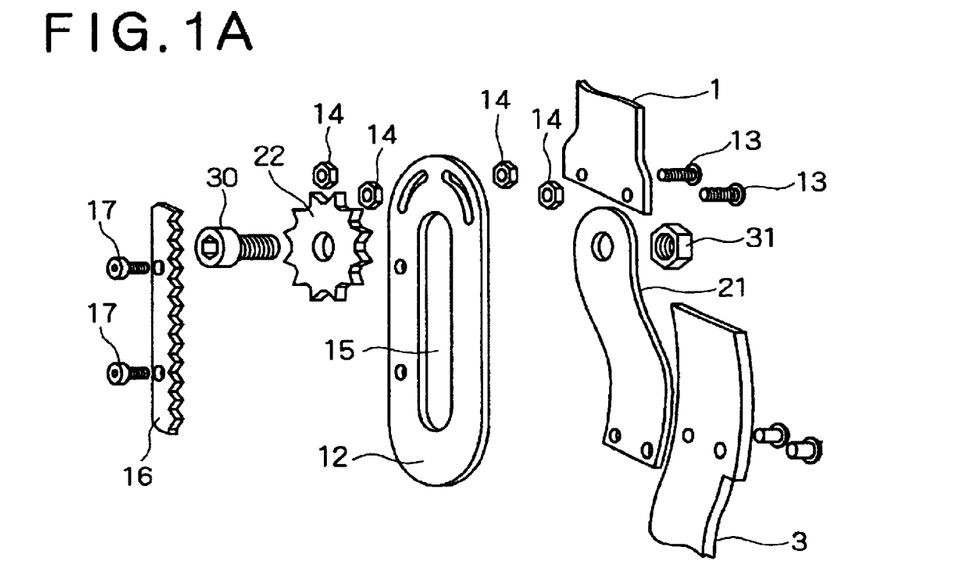
FIG. 1 is an exploded perspective view showing the constitution of an essential portion of a knee brace.
Figure 1B:
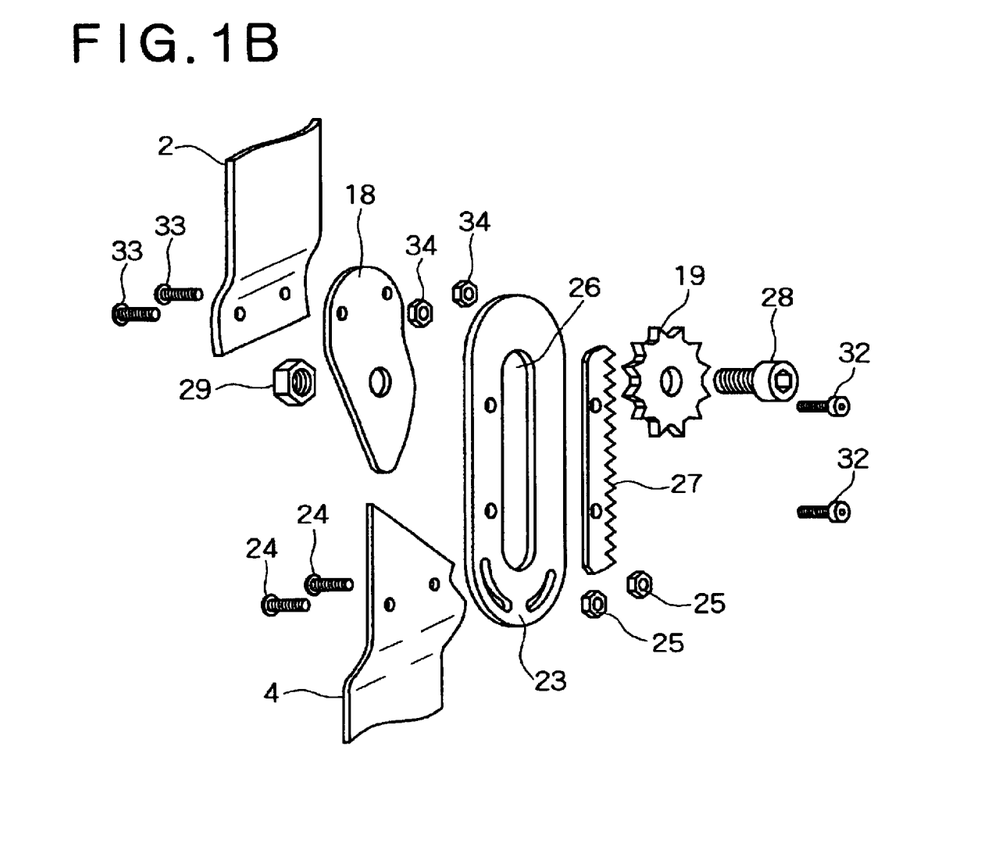
Figure 2:
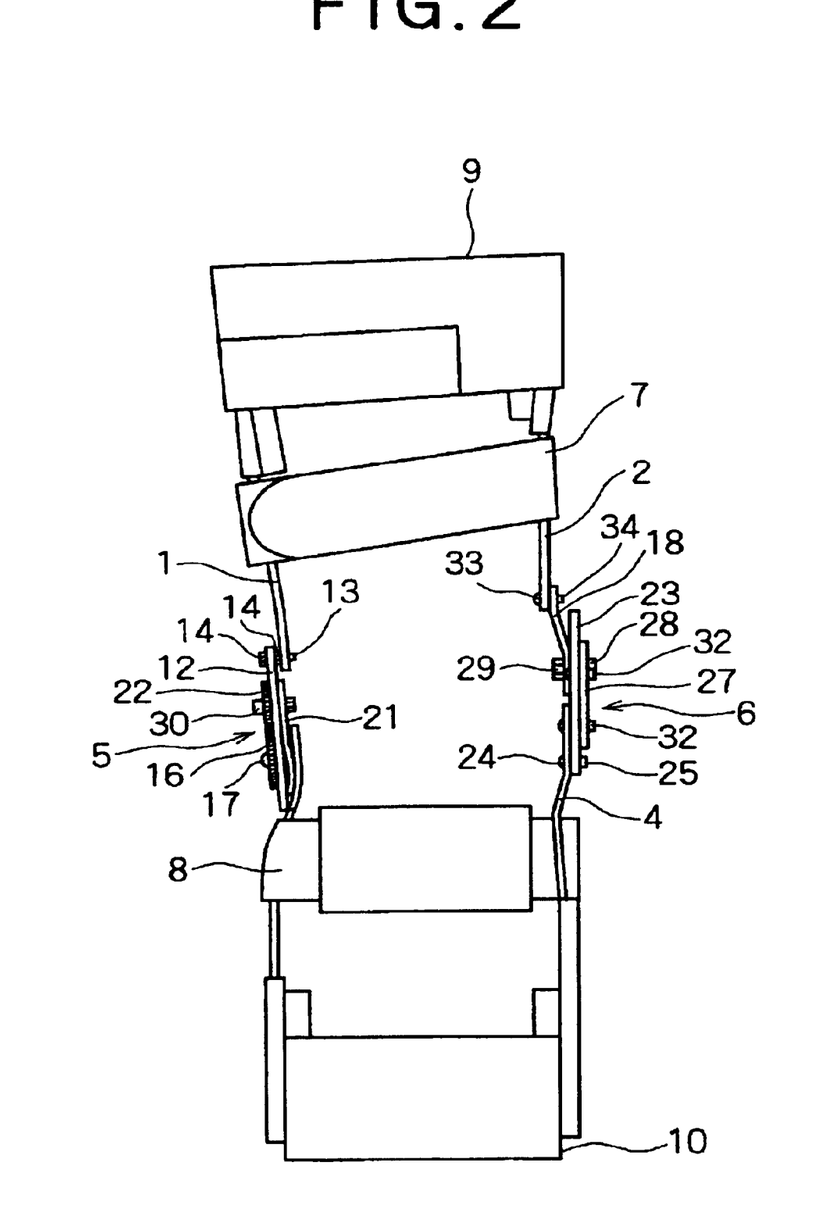
FIG. 2 is a front view showing the knee brace.
Figure 3:
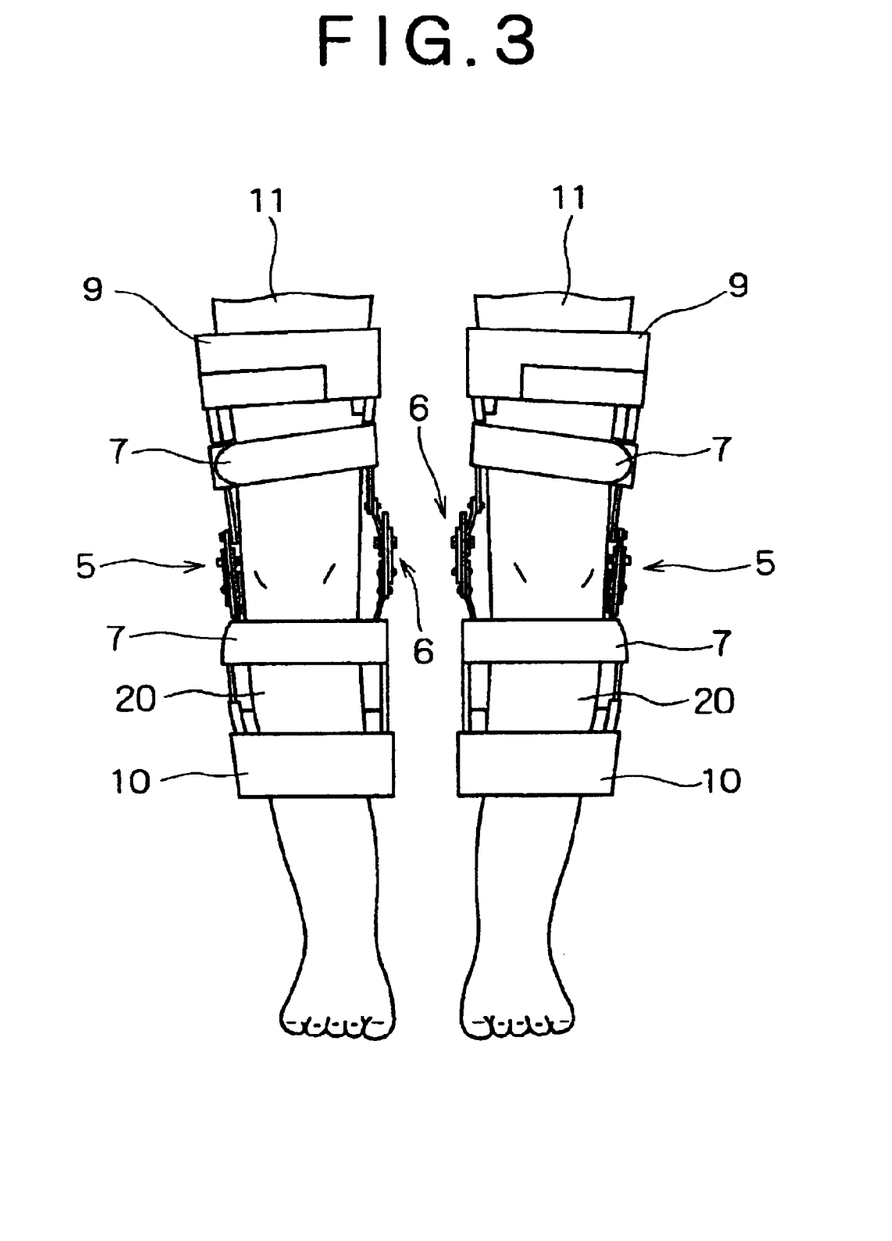
FIG. 3 illustrates an installation state of the knee brace.
Figure 4:
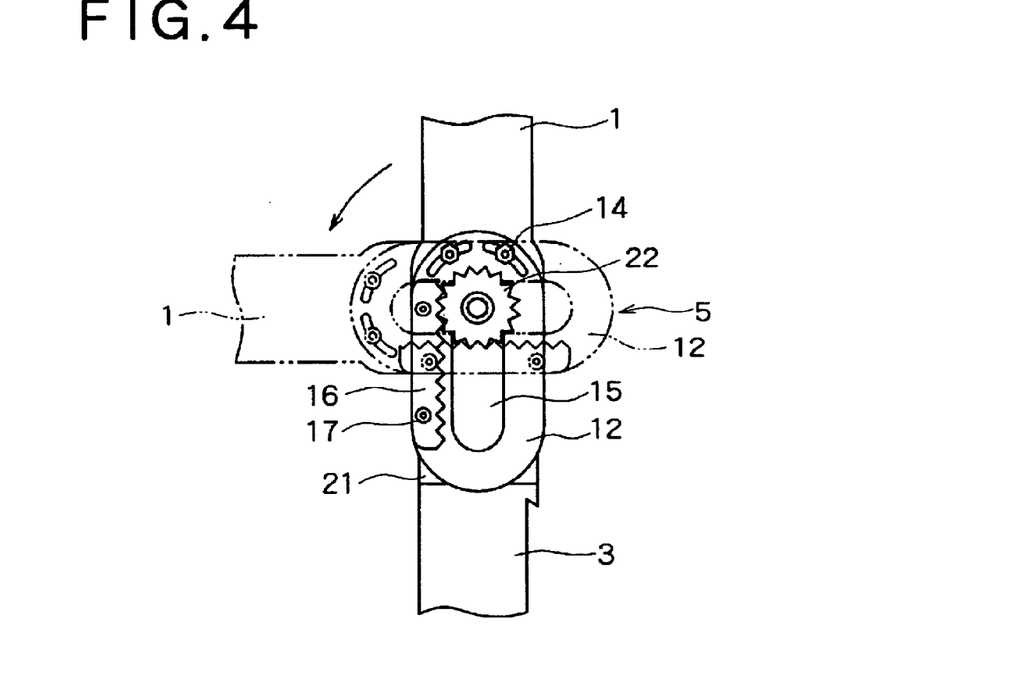
FIG. 4 illustrates an operating state of a hinge device placed on a knee joint lateral portion.
Figure 5:
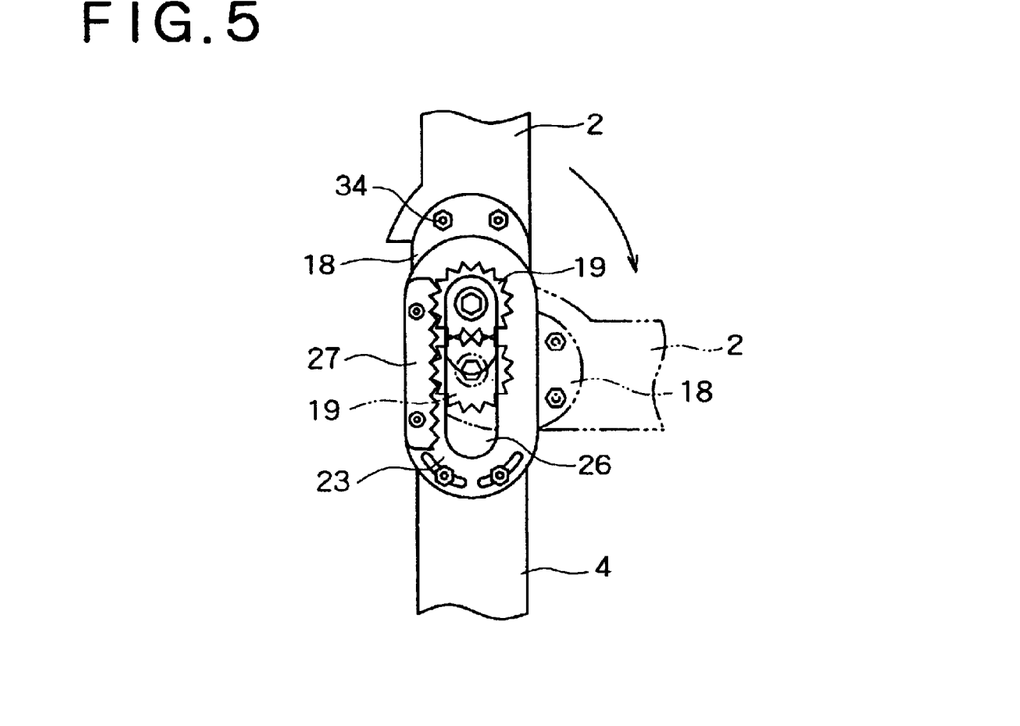
FIG. 5 illustrates an operating state of a hinge device placed on a knee joint medial portion.

FIGS. 1(a) and 1(b) are exploded perspective views showing the constitution of an essential portion of a knee brace, FIG. 2 is a front view showing the knee brace, FIG. 3 illustrates an installation state of the knee brace, FIG. 4 illustrates an operating state of a hinge device placed on a knee joint lateral portion, and FIG. 5 illustrates an operating state of a hinge device placed on a knee joint medial portion. The knee brace shown in these Figures relates to a right leg knee brace installed to a case of degenerative knee arthrosis with the object of giving a corrective treatment. This knee brace comprises first and second arms 1, 2 constituting a pair of left and right arms, third and fourth arms 3, 4 constituting a pair of left and right arms, hinge devices 5, 6, straps 7, 8 and upper and lower cuffs 9, 10.

Each of the first and second arms 1, 2 is made of a material having a rigidity enough to resist a torsional load and a bending load into the shape of a narrow longitudinally-longer flat plate fixable to each of the bilateral sides of a user's thigh 11. The opposite ends of the upper cuff 9 expansive upwards and protrusive rearwards in a semicircular curved shape are mounted to the upper ends of the first and second arms 1, 2 to set up the first and second arms 1, 2 at a distance corresponding to a size of the user's thigh 11. Use of a member characterized by having a low downward frictional resistance and a remarkably high upward frictional resistance, such as a member having downwardly directing fine bristles thickly planted on a surface opposite to the user's thigh 11, for instance, so as to make contact with either of the anterior and posterior sides of the user's thigh 11 is enough for the upper cuff 9. The reason why the upward and downward frictional resistances need to be made different from each other as the characteristics of the inside surface of the upper cuff 9 is as follows. That is, while the thigh 11 makes a smoothly downward motion along the inside of the upper cuff 9 at the time of knee flexion, a contact of the thigh 11 with at least a part of the inside surface of the upper cuff 9 occurs at the time of knee extension. Thus, the thigh 11 acts upwards on the contact surface, in other words, on the upper cuff 9, with the result that upward femur traction is required. The strap 7 is a fastening orthosis for fixing the knee brace to the user's thigh 11. A connection plate 12 is fixedly mounted to the lower end of the first arm 11 with bolts 13 and nuts 14. The connection plate 12 has a longitudinally longer guide groove 15 in parallel to an extension of a centerline of the first arm 1. In addition, a rack 16 is mounted to the connection plate in parallel to a linearly rear-side edge of the guide groove 15 with fastenings 17. It does not matter if the rack 16 extends over a curved rear-side edge of the guide groove 15. An angle adjusting plate 18 gently outward-leaning downwards in conformity with a user's leg medial surface shape is fixedly mounted to the lower end of the second arm 2 with bolts 33 and nuts 34. A gear 19 is fixedly mounted to the outside surface of the angle adjusting plate 18 with a bolt 28 and a nut 29 so as to prevent the gear from being turned.

Each of the third and fourth arms 3, 4 is made of a material having a rigidity enough to resist a torsional load and a bending load into the shape of a narrow longitudinally-longer flat plate fixable to each of the bilateral sides of the user's shank 20 in a similar manner to the first and second arms 1, 2. The opposite ends of the lower cuff 10 protrusive forwards in a semicircular curved shape are mounted to the lower ends of the third and fourth arms 3, 4 to set up the third and fourth arms 3, 4 at a distance corresponding to a size of the user's shank 20. The strap 8 is a fastening orthosis for fixing the knee brace to the user's shank 20. The strap 8 and the lower cuff 10 are formed to meet a demand for close contact with the user's shank 20. This is because the shanks 20 need to act as supporting points for upward traction of the thighs 11 against the shanks 20. An angle adjusting plate 21 gently outward-leaning upwards in conformity with a user's leg lateral surface shape is fixedly mounted to the upper end of the third arm 3. In addition, a gear 22 is fixedly mounted to the outside surface of the angle adjusting plate 21 with a bolt 30 and a nut 31 so as to prevent the gear from being turned. A connection plate 23 is fixedly mounted to the upper end of the fourth arm 4 with bolts 24 and nuts 25. The connection plate 23 has a longitudinally longer guide groove 26 in parallel to an extension of a centerline of the fourth arm 4. A rack 27 is mounted to the connection plate in parallel to a linearly front-side edge of the guide groove 26 with fastenings 32.

The gears 22, 19 are mounted in the guide grooves 15, 26 so as to be capable of sliding while being in mesh with the racks 16, 27 respectively. The first arm 1 is pivotally connected to the third arm 3, while the second arm 2 is pivotally connected to the fourth arm 4 to provide two pairs of upper and lower arms. The gears 22, 19 are formed in mesh with the racks 16, 27 on condition that the gears 22, 19 are located at the uppermost positions in the guide grooves 15, 26 when the two pairs of upper and lower arms are in extensional position.

An operation of the knee brace according to the above embodiment will now be described. As shown in FIG. 3, the knee braces are installed to the lower limbs by tightly putting the straps 7, 8 on the thighs 11 and the shanks 20 respectively after location of each knee brace such that the hinge devices 5, 6 are placed at the knee bilateral sides by facing the anterior side of the user's shank 20 to the back of the lower cuff 10, while facing the posterior side of the user's thigh 11 to the front of the upper cuff 9. When the user flexes one's knees with the knee braces on, the first and second arms 1, 2 are tilted rearwards by the hinge devices 5, 6 and are further pivotally moved for transformation into a flat shape. When the two pairs of upper and lower arms are in extensional position, the gears 22, 19 are located at the uppermost positions in the guide grooves 15, 26. On the other hand, when the first and second arms 1, 2 are pivotally moved rearwards, the positions of the gear 19 and the connection plate 12 are shifted. In other words, when the first and second arms 1, 2 constituting the pair of left and right arms are tilted rearwards from a standing position further into a flattening position, a rearward tilting movement of the rack 16 together with the connection plate 12 as shown in FIG. 4 occurs in the hinge device 5, which then transmits the motive power to the gear 22 through the rack 16. In this place, since the gear 22 is fixedly mounted to the third arm 3 through the angle adjusting plate 21, the hinge device 5 transmits the motive power of the rack 16 to the connection plate 12 to shift the connection plate 12 rearwards with respect to the gear 22, with the result that the guide groove 15 is allowed to shift so as to put the gear 22 in a direction opposite to the side of the first arm 1 in the guide groove 15.

In addition, a pivotal movement of the gear 19 together with the angle adjusting plate 18 and the second arm 2 occurs in the hinge device 6, which then transmits the motive power to the rack 27, as shown in FIG. 5. In this place, since the rack 27 is fixedly mounted to the fourth arm 4, the gear 19 is allowed to shift from the uppermost position in the guide groove 26 downwards (toward the fourth arm 4) by the same distance as an amount of circumferential movement attributable to the pivotal movement of the gear 19, while being in mesh with the rack 27.

When the state of the knees is shifted from flexion to extension, the first and second arms 1, 2 are allowed to pivotally move by the hinge devices 5, 6 from the flattening position to the standing position. An operating state of the hinge device 5 placed on the user's leg lateral side to connect the first arm 1 and the third arm 3 together will now be described. When the connection plate 12 having the guide groove 15 and fixedly mounted to the first arm 1 is placed in the standing position together with the first arm 1, the motive power of the rack 16 is transmitted to the gear 22. In this place, since the gear 22 is fixedly mounted to the angle adjusting plate 21 so as to prevent the gear from being pivotally moved, the motive power of the rack 16 is transmitted to the connection plate 12 to shift the connection plate 12 downwards, with the result that the gear 22 is placed at the uppermost position in the guide groove 15. In this case, although the position of the gear 22 in the guide groove 15 is shifted, it is supposed to be a shift originally based on the pivotal movement of the connection plate 12, so that a distance between the lower end of the first arm 1 and the upper end of the third arm 3 almost remains unchanged.

In addition, an operating state of the hinge device 6 will now be described. When the second arm 2 is pivotally moved to the standing position, the gear 19 fixedly mounted to the second arm 2 is allowed to pivotally move together with the second arm 2. In this case, the gear 19 is shifted upwards within the guide groove 26 to the uppermost position in the guide groove 26, while being in mesh with the rack 27. Thus, the lower end of the second arm 2 is allowed to shift upwards to a position apart from the upper end of the fourth arm 4.

Use of the knee braces according to the present embodiment permits the knee joint medial portions mounted with the hinge devices 6 to perform upward traction of only the femurs with the tibias fixed, without permitting the knee joint lateral portions mounted with the hinge devices 5 to perform traction of the femurs and the tibias, and as a result, produces an effect of correcting a genu varum characterized by a medial-part forced contact state of the femurs against the tibias. In addition, the hinge devices 5 are operated as supporting points, so that the hinge devices 6 have a function of rotating the shanks 20 from the anterior side to a position off to the superolateral side.

In addition, in a process of a walking action from flexion of the knees for forward push of the lower limbs till touch of the heels on the ground, the shanks 20 make traction, eversion and rotation against the thighs 11 as described above. For this reason, the pairs of upper and lower arms 1, 2, 3 and 4 produce a moment in the opposite direction with the hinge devices 5, 6 as supporting points, so that a force acts in the opposite direction. However, since the arms 1, 2, 3 and 4 are made of the material that resists the torsional load and the bending load, a distortion is produced a little. In heel and toe leaving actions as the subsequent walking action, a force in a direction opposite to the above direction acts on the arms 1, 2, 3 and 4 due to the reaction. Thus, the force is applied in a direction of pushing out the lower limbs to thereby make it easy for the user to do a push-out motion in walking.

Although the above embodiment shown in FIGS. 1 to 5 has been described about the genu varum corrective knee brace, it is to be understood that a genu valgum (knock knee) corrective knee brace is realized by providing the hinge devices 5, 6 such that the hinge device 5 is placed on the knee medial side, that is, a joint portion between the second and fourth arms, while the hinge device 6 is placed on the knee lateral side, that is, a joint portion between the first and third arms. It is also to be understood that the genu valgum corrective knee brace is also included in the present invention. The knee braces each characterized by providing the hinge devices 5, 6 between the upper and lower arms such that the hinge device 5 is placed on the knee joint medial side and the hinge device 6 is placed on the knee joint lateral side permit the knee joint lateral portions to perform upward traction of only the femurs with the tibias fixed, without permitting the knee joint medial portions to perform traction of the femurs and the tibias in a case of shifting the state of the knees from flexion to extension, and as a result, produces an effect of correcting the genu valgum (knock knee) characterized by a lateral-part forced contact state of the femurs against the tibias.

Figure 6A:
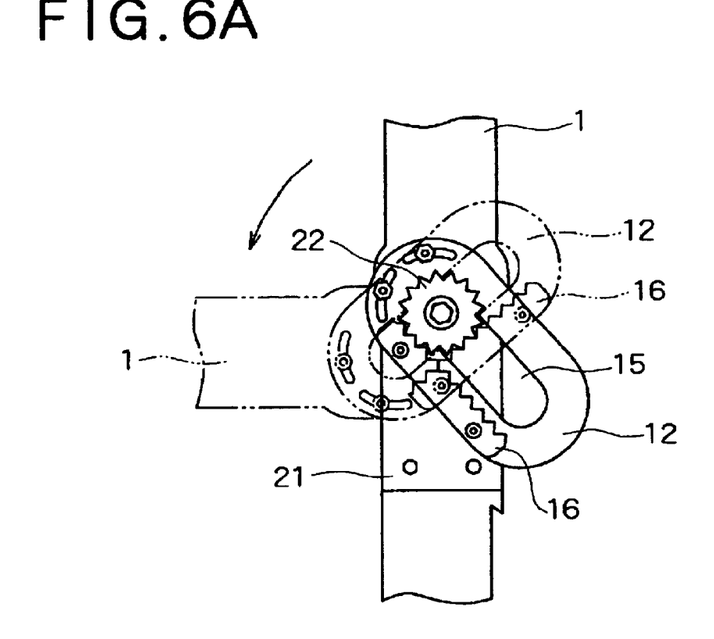
FIG. 6 illustrates an operating state of a hinge device according to a different embodiment.
Figure 6B:
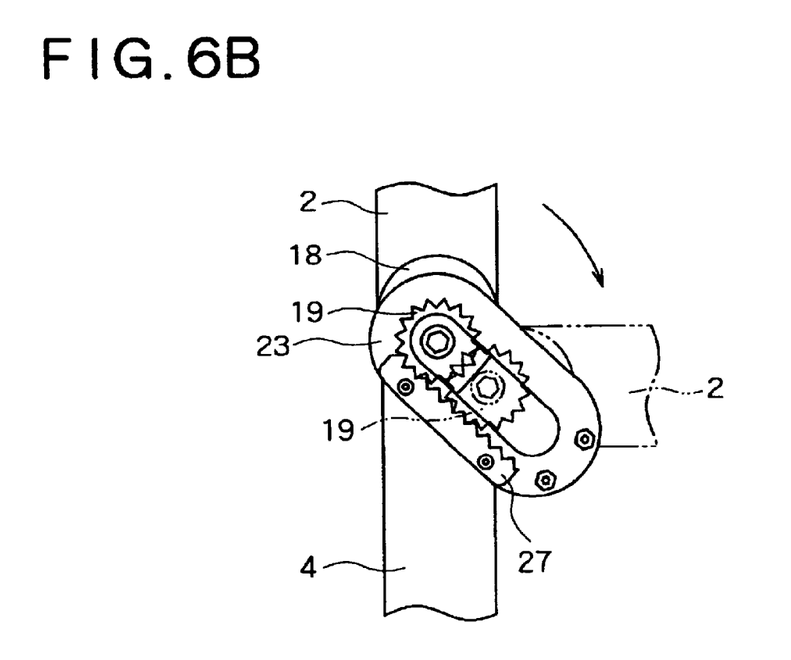

An embodiment shown in FIG. 6 will now be described. FIG. 6(a) illustrates an operating state of a hinge device as viewed from the left, and FIG. 6(b) illustrates an operating state of the hinge device as viewed from the right. A difference between the embodiment shown in FIGS. 1 to 5 and the embodiment shown in FIG. 6 is that the connection plate 12 having the rack 16 and the guide groove 15 and the connection plate 23 having the rack 27 and the guide groove 26 in the embodiment shown in FIG. 6 are fixedly mounted to the first arm 1 and the fourth arm 4 such as to be inclined in the longitudinally opposite directions at the same inclination angle with respect to each extension of the centerlines of the first and fourth arms 1, 4. The knee brace characterized by providing the inclined racks 16, 27 as described above has an effect of correcting an abnormal rotation occuring in flexion and extension of the knees by changing to a normal rotation through fine adjustment or the like of an angle. In addition, it is to be understood that a knee brace characterized in that either the rack 16 or 27 is inclined is also included in the present invention.

Figure 7:
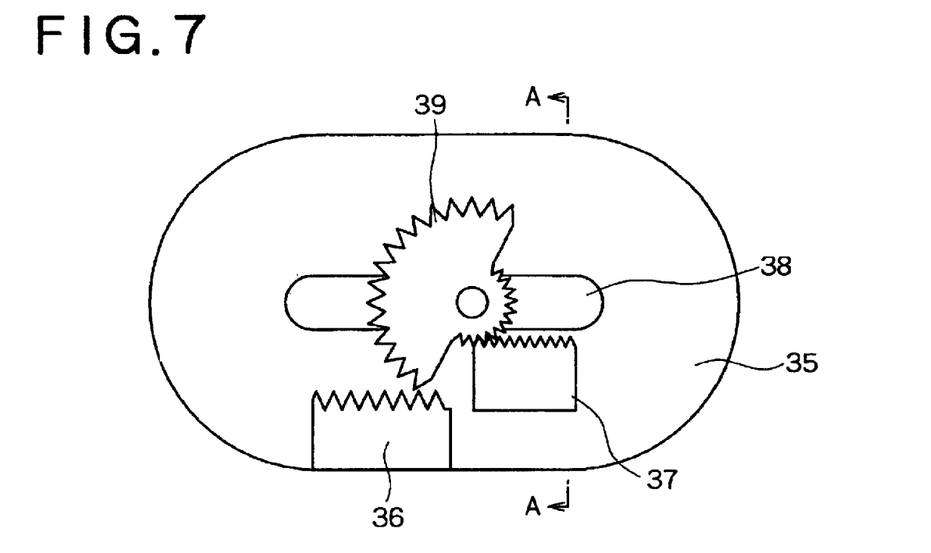
FIG. 7 illustrates a hinge device according to a further different embodiment.
Figure 8:
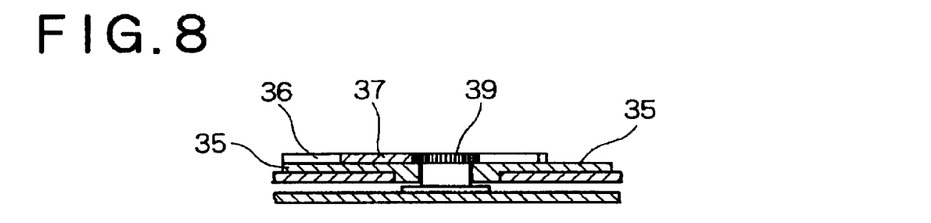
FIG. 8 is a sectional view taken along line A—A of FIG. 7.

FIGS. 7 and 8 are enlarged views showing a hinge device according to a further different embodiment of the present invention. Racks 36, 37 respectively having tooth portions different in tooth pitch are mounted on a connection plate 35 at different levels. A gear 39 having different root radius portions different in circumferential tooth pitch is mounted in a guide groove 38 so as to be in mesh with the racks 36, 37 respectively.

Figure 9:
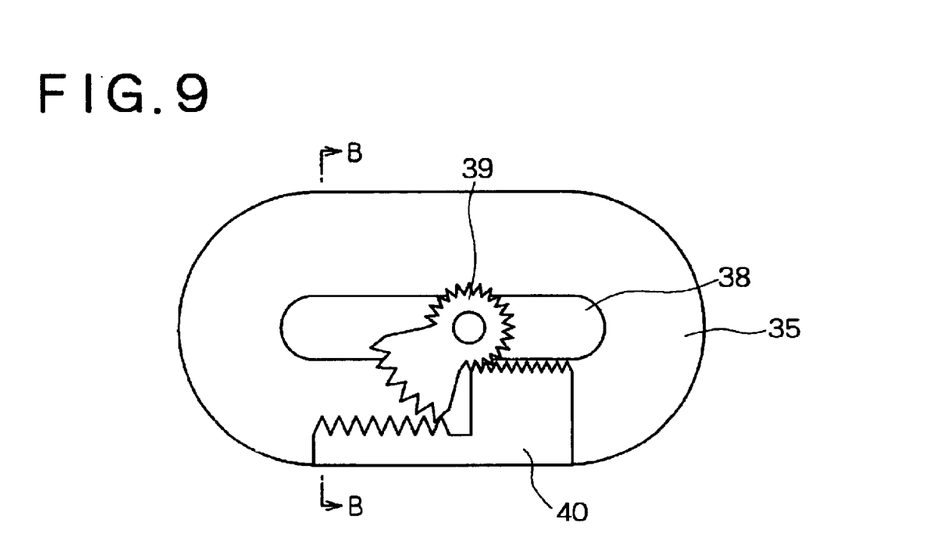
FIG. 9 illustrates a hinge device according to a further different embodiment.
Figure 10:
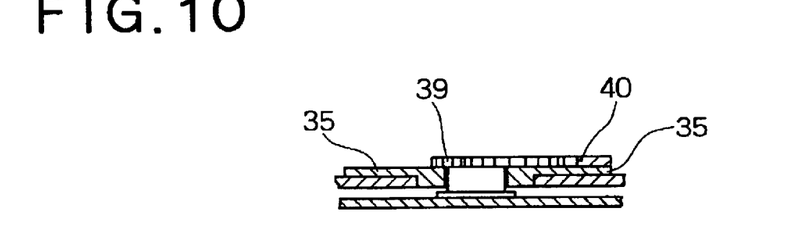
FIG. 10 is a sectional view taken along line B—B of FIG. 9.

FIGS. 9 and 10 illustrate a hinge device according to a further different embodiment of the present invention. For simplification, a description will be given by using like reference numerals for portions having the similar functions to those shown in FIGS. 7 and 8. A rack 40 having different level portions respectively having tooth portions different in tooth pitch is mounted to the connection plate 35. A gear 39 having different root radius portions different in circumferential tooth pitch is mounted in the guide groove 38 so as to be in mesh with the rack 40.

Figure 11:
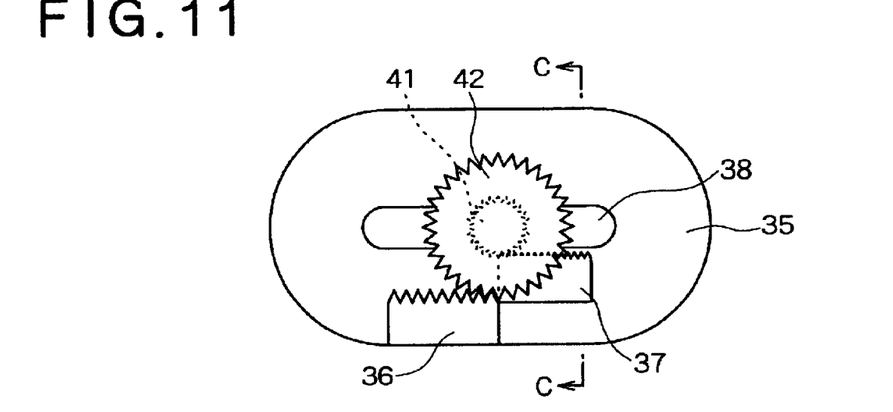
FIG. 11 illustrates a hinge device according to a further different embodiment.
Figure 12:
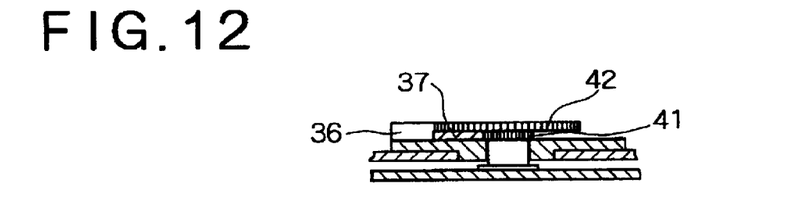
FIG. 12 is a sectional view taken along line C—C of FIG. 11.

FIGS. 11 and 12 illustrate a hinge device according to a further different embodiment of the present invention. Concentric gears 41, 42 are mounted in the guide groove 38. The gears 41, 42 respectively have tooth portions different in circumferential tooth pitch. The gear 42, 41 are formed such that the gear 42 is in mesh with the rack 36, while the gear 41 is in mesh with the rack 37.

Figure 13:
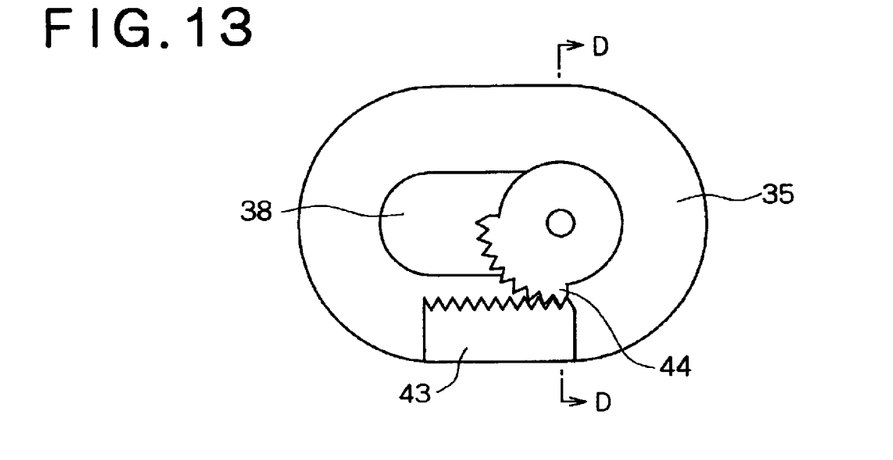
FIG. 13 illustrates a hinge device according to a further different embodiment.
Figure 14:
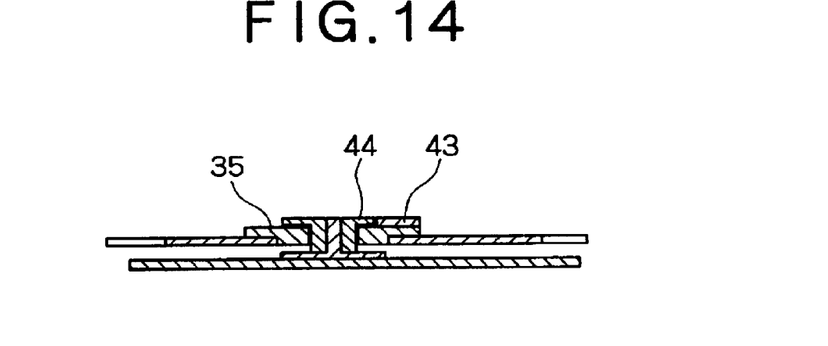
FIG. 14 is a reduced sectional view taken along line D—D of FIG. 13.

FIGS. 13 and 14 illustrate a hinge device according to a further different embodiment of the present invention. A rack 43 is mounted to the connection plate 35, and a gear 44 having a tooth portion only on a part of the circumference is mounted in the guide groove 38 so as to be in mesh with the rack 43.

When the rack is mounted in inclined position at the same inclination angle in the opposite directions on condition that the hinge device realized by varying the position and the size or the like of the gear and the rack as shown in FIGS. 7 to 14 is adopted as the hinge device according to the embodiment shown in FIG. 6, the fine adjustment or the like of a rotation angle may be performed at more accuracy, with the result that it is possible to provide various knee braces suitable to the degree of user's knee troubles. It is a matter of course that the hinge device realized by varying the position and the size or the like of the rack and the gear as shown in FIGS. 7 to 14 may be also applied to the hinge device characterized in that either the rack is inclined.

Figure 15:
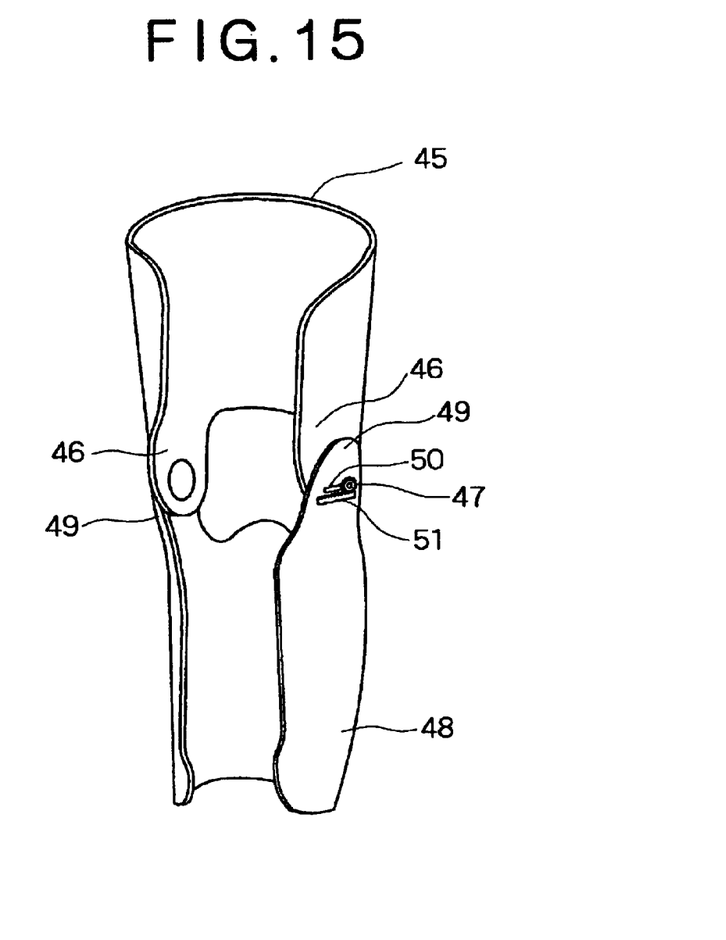
FIG. 15 is a perspective view showing a knee brace according to a further different embodiment.
Figure 16:
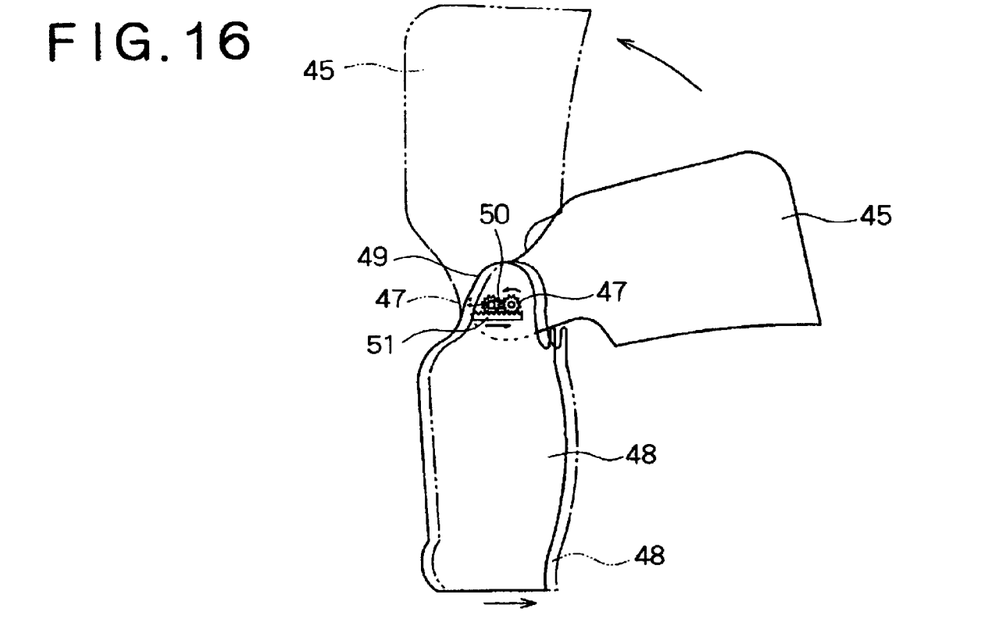
FIG. 16 is a side view showing an operating state of the knee brace.

An embodiment shown in FIGS. 15 and 16 will now be described. A pair of gear mounting pieces 46 facing each other is provided as a result of downwardly extending the left and right sides of a thigh holding part 45 having a strap (not shown). A gear 47 is fixedly mounted to the outside of each gear mounting piece 46 so as to prevent the gear from being turned. A pair of guide groove formation pieces 49 is also provided as a result of upwardly extending the left and right sides of a shank holding part 48 having a strap (not shown). Each guide formation piece 49 has a laterally longer guide groove 50 orthogonal to a user's tibia axial centerline, and a rack 51 is mounted to each guide formation piece in parallel to the linear lower-side edge of the guide groove 50. The gear 47 is in mesh with the rack 51 such that the thigh holding part 45 is inclined rearwards at an angle of about 90 degrees with respect to the shank holding part 48 to put the gear 47 at a rear portion in the guide groove 50.

An operation of the knee brace according to the above embodiment will now be described with reference to FIG. 16. When the thigh holding part 45 inclined rearwards with respect to the shank holding part 48 as shown by a solid line in FIG. 16 is shifted to a position where the thigh holding part 45 extends in alignment with the shank holding part 48, the gear 47 is allowed to pivotally move in a direction shown by an arrow in FIG. 16 together with the thigh holding part 45, while the rack 51 is allowed to shift backwards together with the shank holding part 48. In a case of extending the knees having suffered damages such as anterior cruciate amputation, the shanks are apt to be advanced. On the other hand, use of the knee braces according to the present embodiment makes it possible to correct the shanks so as to be put to their normal positions through the backward movement of each shank holding part 48 at the time of knee extension.

An embodiment shown in FIG. 17 will now be described. For simplification, a description will be given by using like reference numerals to portions having the similar functions to those shown in FIGS. 15 and 16. A rack 52 is mounted in parallel to a linear upper-side edge of the guide groove 50 formed in each of the pair of guide groove formation pieces 49. The gear 47 is in mesh with the rack 52 such that the thigh holding part 45 is inclined rearwards at an angle of about 90 degrees with respect to the shank holding part 48 to put the gear 47 in a front portion in the guide groove 50.

Figure 17:
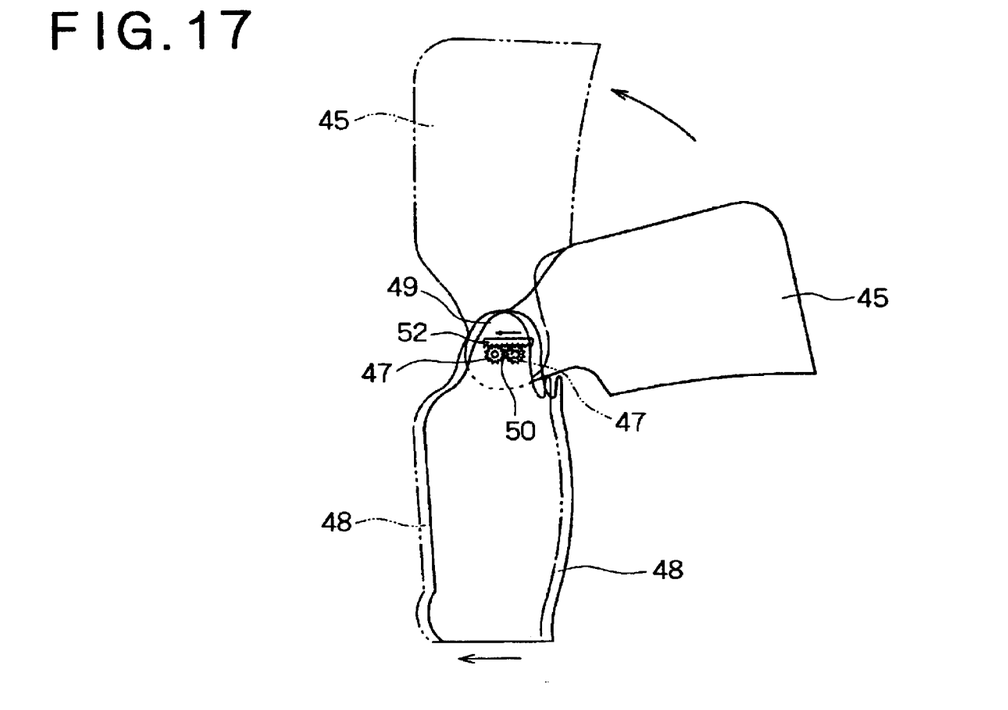
FIG. 17 is a side view showing an operating state of a knee brace according to a further different embodiment.

Then, when the state of the knees is shifted from flexion to extension with the knee braces installed to the lower limbs using straps (not shown), the gear 47 is allowed to pivotally move in a direction shown by an arrow in FIG. 17 together with the thigh holding part 45, while the rack 52 is allowed to shift forwards together with the shank holding part 48. In a case of extending the knees having suffered damages such as posterior cruciate amputation, the shanks are apt to be retracted. On the other hand, use of the knee braces according to the present embodiment makes it possible to correct an abnormal retraction of the shanks through an operation of each shank holding part 48 to advance the shanks at the time of knee extension.

Figure 18:
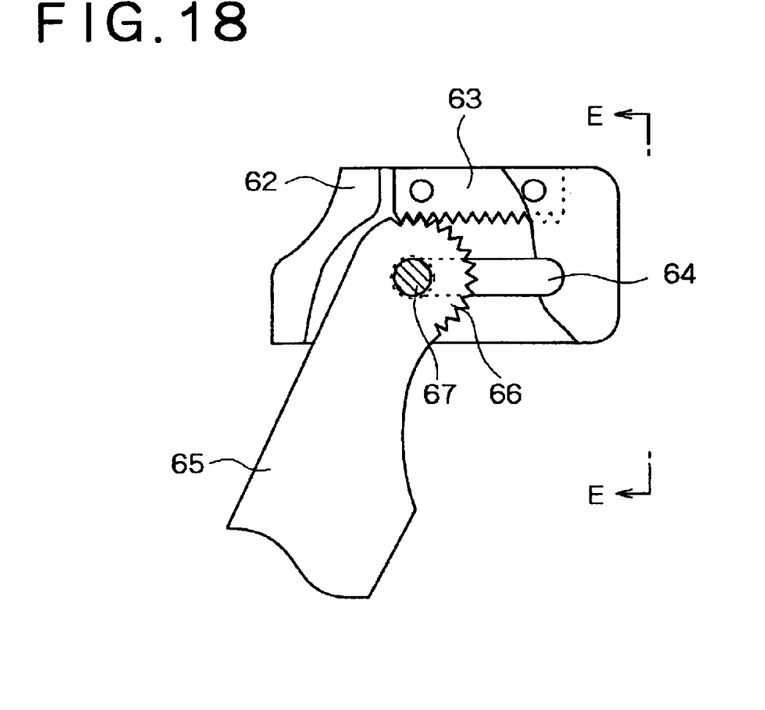
FIG. 18 is a fragmentary broken view showing a hinge device according to a further different embodiment.
Figure 19:
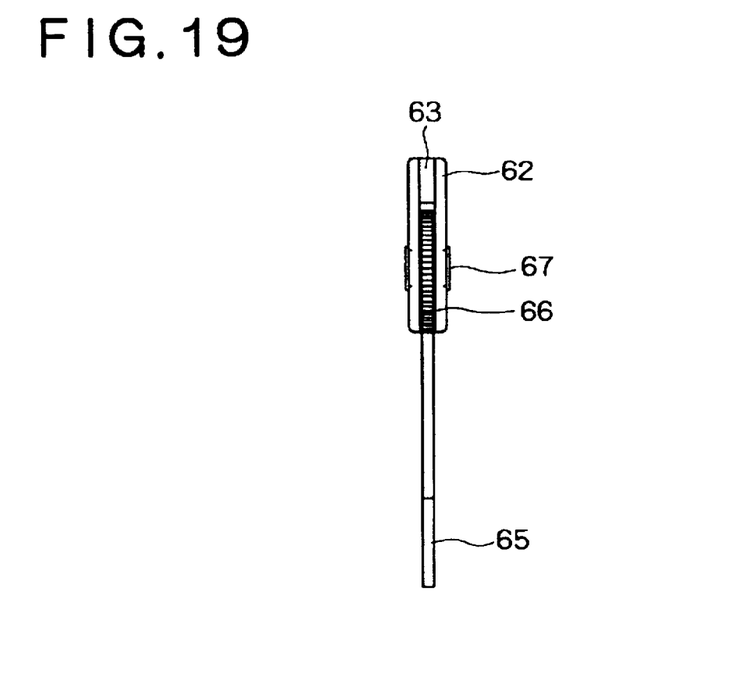
FIG. 19 is a view taken along line E—E of FIG. 18.

An embodiment shown in FIGS. 18 and 19 will now be described. A guide groove 64 having a rack 63 is provided in a lower portion of an upper arm 62 having an upper cuff (not shown) and a strap (not shown). A gear 66 meshing with the rack 63 is formed at the end of a lower arm 65 having a lower cuff (not shown) and a strap (not shown). In addition, a pivot 67 having a flange is provided in the side of the lower arm. The lower portion of the upper arm 62 has an insertion groove on the inside. Thus, the upper end of the lower arm 65 is mounted in the insertion groove such that the gear 66 is in mesh with the rack 63 while the pivot 67 is pivotally moved in the guide groove 64 so as to be capable of sliding.

Figure 20:
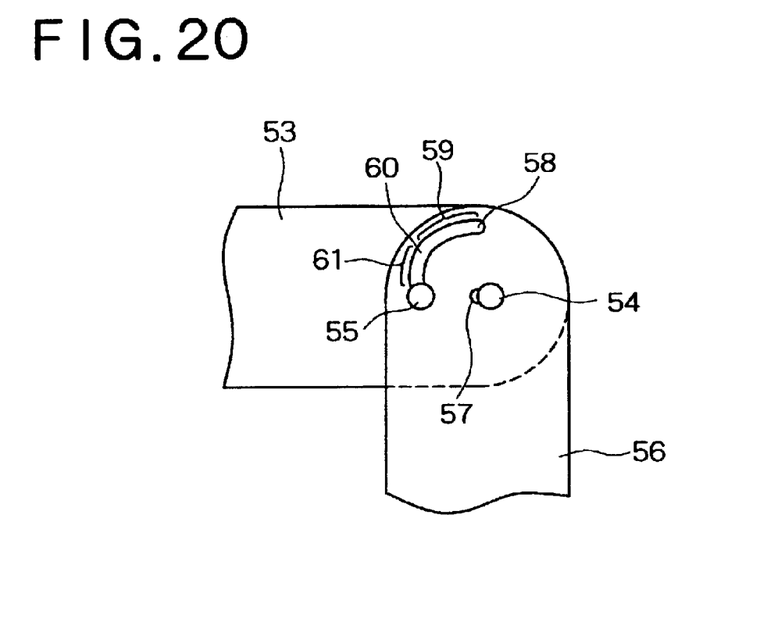
FIG. 20 illustrates an operating state of a hinge device according to a further different embodiment.
Figure 21:
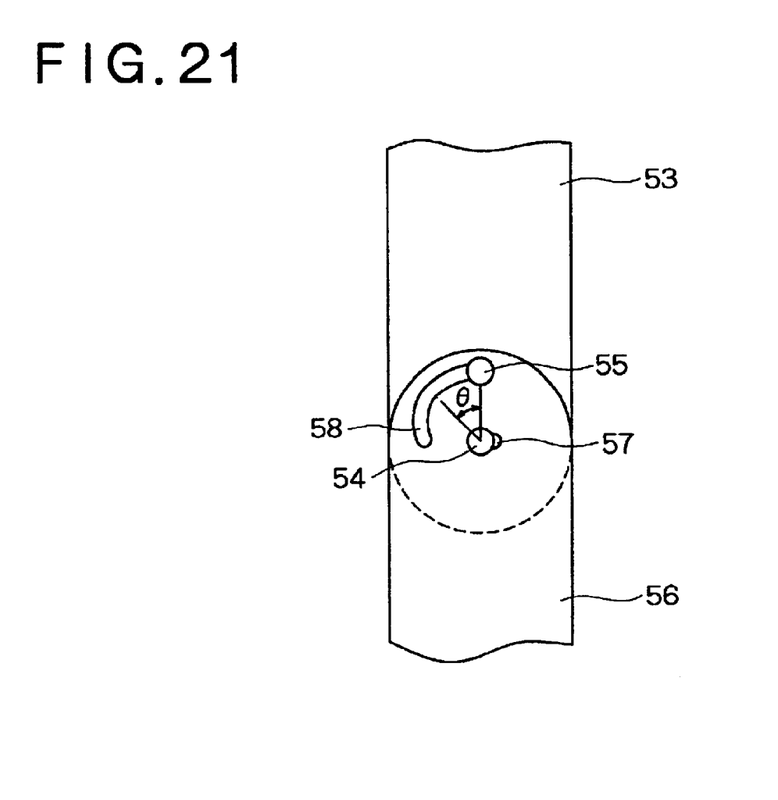
FIG. 21 illustrates an operating state of the hinge device.

An embodiment shown in FIGS. 20 and 21 will now be described. A knee brace according to this embodiment is realized with the object of alleviating a knee pain caused in a case of flexion and extension of the knees by reason of aging or the like. A first projection 54 and a second projection 55 are provided on the lower outside surface of each of the upper arms 53 constituting a pair of left and right arms. Each of the lower arms 56 constituting a pair of left and right arms has a first guide groove 57, which allows the first projection 54 to slide, and a second guide groove 58, which allows the second projection 55 to slide. The second guide groove 58 is composed of a semicircular portion 59, a bent portion 60 and a curved portion 61 in communication with one another. The upper and lower arms 53, 56 respectively have straps (not shown) to make each knee brace installable to the lower limbs. The bent portion 60 is provided such that an angle θ made by a front end of the semicircular portion 59 and the bent portion 60 with the first projection 54 as the center when the first projection 54 is placed at the rear end of the first guide groove 57 agrees with a bending angle that causes pain to the knees in a case of shifting the state of the user's knees from extension to flexion. In addition, a linear distance between the front end of the semicircular portion 59 and the rear end of the first guide groove 57 is set to be equal with a linear distance between the lower end of the curved portion 61 and the front end of the first guide groove 57.

An operation of the knee brace according to the above embodiment will now be described. The knee braces according to this embodiment are installed to the lower limbs using the straps (not shown) such that pivotal parts of the upper and lower arms are placed on the knee bilateral sides. As shown in FIG. 20, when the knees are in the flexion state, the first projection 54 is located at the front end of the first guide groove 57, while the second projection 55 is located at the lower end of the curved portion 61 of the second guide groove 58. On the other hand, in a case of shifting the state of the knees from flexion to extension, the upper arm 53 is allowed to pivotally move upwards with the first projection 54 as the center, while the second projection 55 is allowed to slide toward the bent portion 60 within the curved portion 61 of the second guide groove 57. When the extension state of the knees is kept after the second projection 55 reaches the bent portion 60 which provides the bending angle that causes pain to the knees, the first projection 54 is allowed to shift rearwards within the first guide groove 57. Thus, the positions of the first projection 54 and the second projection 55 are shifted as shown in FIG. 21 respectively through the movement with the rear end of the first guide groove 57 as the center and the slide movement within the semicircular portion 59 of the second guide groove 58, while the femurs are subjected to upward traction together with the upper arms 53.

In a case of knee extension that causes pain to the knees, the knee brace according to the above embodiment has an effect of permitting the knee extension without causing pain to the knees, simultaneously with the upward femur traction.

Figure 22:
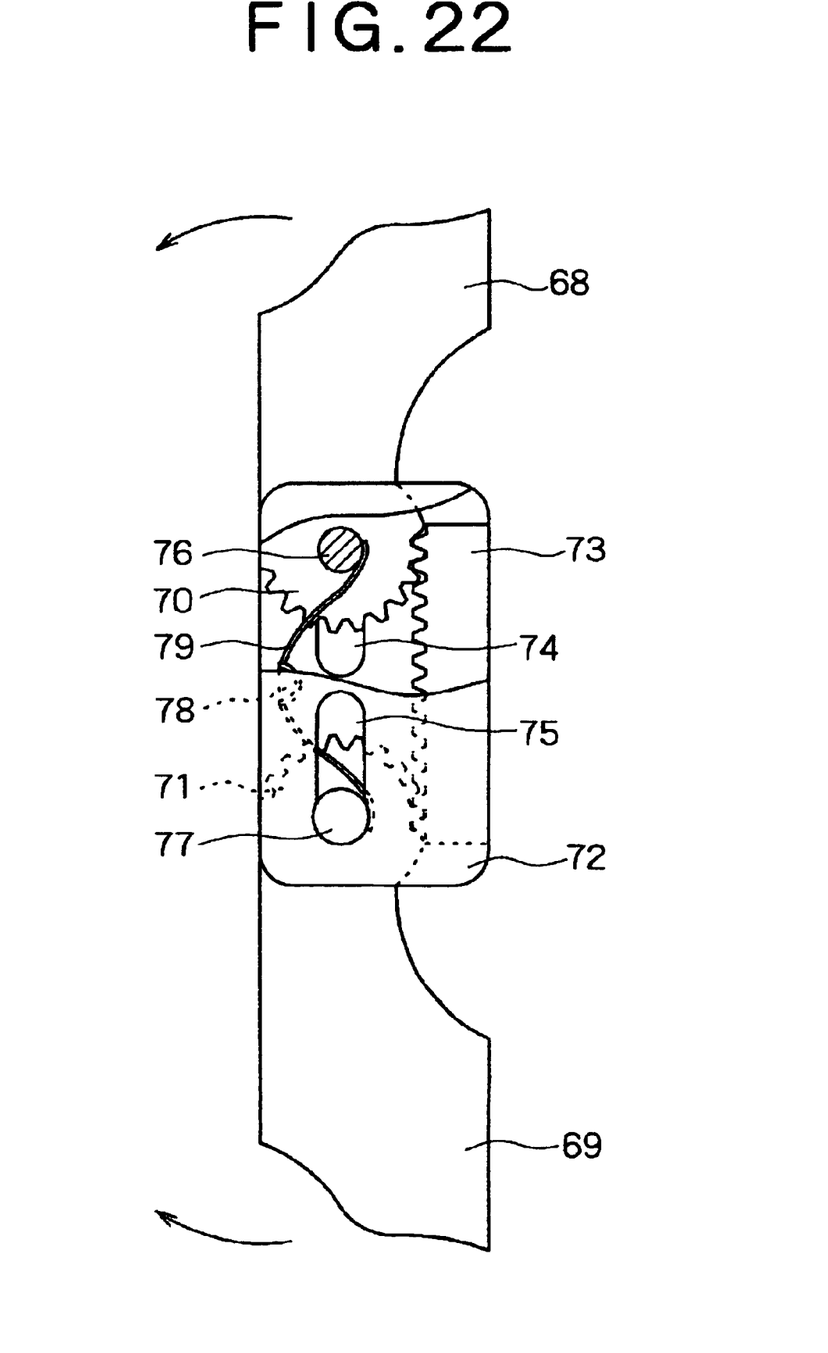
FIG. 22 is a fragmentary broken view showing an essential portion of a knee brace according to a further different embodiment.

An embodiment shown in FIG. 22 will be now described. A gear 70 is formed at a lower end of an upper arm, while a gear 71 is formed at an upper end of a lower arm 69. A connection plate 72 has an insertion groove having a rack 73 on the inside. The connection plate 72 also has longitudinal guide grooves 74, 75. In the insertion groove, the gears 70, 71 are in mesh with the rack 73, and pivots 76, 77 are provided so as to be capable of sliding while being pivotally moved in the guide grooves 74, 75. The connection plate 72 also has an axis 78, and an elastic piece 79 is wound around the axis 78. The opposite ends of the elastic piece 79 are allowed to make contact with the peripheries of the pivots 76, 77 to energize the ends of the upper arm 68 and the lower arm 69 so as to be apart from each other.

Although the present invention has been described as related to the embodiments of the knee brace realized by using the gears and the racks together with the projections and the guide grooves for performing traction of the thigh holding part, or pivotally moving the thigh holding part while performing the traction, or rotating or moving forwards or backwards the shank holding part, it is to be understood that the present invention is not limited to the above embodiments, and elbow or shoulder joint braces realized by adopting the principle of the present invention are also included in the present invention. In addition, it is also to be understood that all the knee braces having the similar functions to those of the present invention are also included in the present invention.

According to the present invention, since the guide groove having the gear and the rack is provided at each of the bilateral positions of the pair of upper and lower arms, the knee brace of the present invention has an effect of performing traction of only a required portion by a required value using a desired angle for setting a traction peak period for the case of degenerative knee arthrosis such as knock knee and bow leg.

In addition, the knee brace of present invention has also an effect of correcting the abnormal angle made by the thigh and the shank due to collateral ligament damages of the knees and bending to varus or valagus position due to the degenerative knee arthrosis so as to put the thigh and the shank to the zero-degree position between varus and valgus with more accuracy.

In addition, the knee brace of the present invention has also an effect of providing various knee braces suitable to the degree of individual user's knee troubles by varying the radius and the pitch or the like of the gear and the rack.

In addition, the knee brace of the present invention has also an effect of making the fine adjustment or the like of the tibia rotation angle with more accuracy while performing the femur traction by adopting the inclined rack or racks.

In addition, the knee brace of the present invention has also an effect of correcting the abnormal shank advancement or retraction due to the anterior or posterior crusiate damages or the like by providing the pair of left and right gears facing each other at the lower portions of the thigh holding part, while providing the shank holding part having, at its upper portion, the guide groove having the rack.

In addition, the knee brace of the present invention has also an effect of alleviating the pain through the pivotal movement while performing the upward femur traction within the painful knee pivotal range by providing the two pieces of projections on the outside surface of the thigh holding part, while providing the shank holding part having the longitudinal guide groove and the guide groove having portions different in arc center.

In addition, the knee brace of the present invention has also an effect of performing smooth traction by providing the means for energizing the upper and lower arms so as to be apart from each other, while forming the gears at the ends of the pair of upper and lower arms for pivotal connection to the guide grooves provided in the connection plate.

In addition, use of the knee brace of the present invention has a great effect of putting off a period of a surgical operation, and besides, eliminating the need for the operation according to the circumstantances.

What is claimed is:

1. A knee brace comprising:
   a thigh fixing device configured to fix a thigh in position;
   a shank fixing device configured to fix a shank in position; and
   at least one pivotal joint device pivotally connecting the thigh and shank fixing devices on one side of a knee so as to permit flexion and extension of the knee, the at least one pivotal joint device comprising at least one gear configured to slide within at least one guide groove while meshing with at least one rack.

2. A knee brace according to claim 1, wherein the at least one gear is attached to the thigh fixing device and the at least one guide groove is provided in the shank fixing device.

3. A knee brace according to claim 1, wherein the at least one gear is attached to the shank fixing device and the at least one guide groove is provided in the thigh fixing device.

4. A knee brace according to claim 1, wherein the at least one pivotal joint device comprises a plate in which the at least one guide groove is provided and to which the at least one rack is attached.

5. A knee brace according to claim 1, wherein the at least one pivotal joint device comprises two pivotal joint devices configured to be positioned on either side of the knee.

6. A knee brace according to claim 1, wherein the at least one guide groove is extending along at least one of a femur axial center and a tibia axial center.

7. A knee brace according to claim 5, wherein the two pivotal joint devices comprises a first pivotal joint device and a second pivotal joint device, the first pivotal joint device comprises a first gear attached to the thigh fixing device and a first guide groove is provided in the shank fixing device, and the second pivotal joint device comprises a second gear attached to the shank fixing device and a second guide groove provided in the thigh fixing device.

8. A knee brace according to claim 7, wherein the first and second guide grooves are inclined at a substantially same inclination angle in opposite directions.

9. A knee brace according to claim 1, wherein the at least one gear has at least one of different root radius portions and portions different in circumferential tooth pitch, and the at least one rack is provided at different levels, has portions different in tooth pitch corresponding to the circumferential tooth pitch of the at least one gear, or combination thereof.

10. A knee brace according to claim 1, wherein the at least one gear includes a plurality of concentric gears different in circumferential tooth pitch, and the at least one rack has different level portions formed correspondingly to a difference in root radius between the concentric gears, and has tooth portions formed at a substantially same pitch as the circumferential tooth pitch of the at least one gear meshing with the at least one rack.

11. A knee brace according to claim 1, wherein the thigh fixing device and shank fixing device each comprise at least one arm to which the at least one pivotal joint device is attached.

12. A knee brace according to claim 1, wherein the thigh fixing device and shank fixing device comprise thigh and shank cuffs for attaching the thigh fixing device and shank fixing device to the thigh and shank, respectively.

13. A knee brace according to claim 1, wherein the thigh fixing device and shank fixing device comprise thigh and shank straps for attaching the thigh fixing device and shank fixing device to the thigh and shank, respectively.

14. A knee brace according to claim 1, wherein the at least one pivotal joint device is configured to provide femur and tibia traction in vertically opposite directions against at least one of medial and lateral portions of the knee.

15. A knee brace according to claim 1, wherein the at least one pivotal joint device is configured to control and correct a rotation in a femur-to-tibia joint.

16. A knee brace according to claim 1, wherein the at least one pivotal joint device is configured to correct a tibia position with respect to a femur by adjusting a tibia motion when the knee extends.

17. A knee brace according to claim 1, wherein the thigh fixing device comprises first and second arms fixable to bilateral sides of the thigh along a femur, the shank fixing device comprises third and fourth arms fixable to bilateral sides of the shank along a tibia, the first and second arms have lower end portions corresponding to upper end portions of the third and fourth arms, the lower end portions of the first and second arms are pivotally connected to the upper end portions of the third and fourth arms such that the third and fourth arms pivotally move with the at least one pivotal joint device along with knee motion, the at least one gear is provided on one of the lower end portions of the first and second arms or one of the upper end portions of the third and fourth arms, the at least one guide groove is provided in one of the first, second, third and fourth arms which is pivotally connected to the one provided with the at least one gear as a pair, and the at least one guide groove is extending in parallel to an axial center of the femur or the tibia.

18. A knee brace according to claim 17, wherein the at least one pivotal device comprises two pivotal devices, and the first and second arms are pivotally connected to the third and fourth arms via the two pivotal devices, respectively.

19. A knee brace according to claim 1, further comprising a connection plate, wherein the thigh fixing device comprises an upper arm fixable to the thigh along a femur, the shank fixing device comprises a lower arm fixable to the shank along a tibia, the at least one rack is mounted to the connection plate in parallel to the at least one guide groove, and the upper arm has an elastic piece and the at least one gear at a lower end portion of the upper arm, and the lower arm has an upper portion pivotally connected to the lower portion of the upper arm so as to mesh the at least one gear with the at least one rack, and the elastic piece has opposite end portions which slidably make contact with pivots of the at least one pivotal device to energize the ends of the upper and lower arms connected through the connection plate so as to be drivable apart from each other.

20. A knee brace according to claim 1, wherein the at least one gears comprises two gears, the thigh fixing device is configured to accommodate the thigh therein and has a pair of gear mounting portions facing each other on lower left and right side portions of the thigh fixing device such that the two gears are fixedly mounted to the opposite positions on the outsides of the gear mounting portions, the at least one guide groove comprises two guide grooves, the shank fixing device is configured to accommodate the shank therein and has a pair of guide groove formation portions on upper left and right side portions of the shank fixing device such that the two guide grooves are provided in the guide groove formation portions, respectively, in a direction orthogonal to a tibia axial centerline.

21. A joint brace comprising:
- a first limb fixing device configured to fix a first limb in position;
- a second limb fixing device configured to fix a second limb in position;
- at least one pivotal joint device pivotally connecting the first and second limb fixing devices on one side of a joint so as to permit flexion and extension of the joint, the at least one pivotal joint device comprising at least one gear configured to slide within at least one guide groove while meshing with at least one rack.

* * * * *